United States Patent [19]

Dixon et al.

[11] Patent Number: 4,645,834
[45] Date of Patent: Feb. 24, 1987

[54] SYNTHESIS OF HETEROCYCLIC AMINES VIA THE REACTION OF DIALKYLENE GLYCOL AND AMMONIA

[75] Inventors: Dale D. Dixon, Kutztown, Pa.; Randall J. Daughenbaugh, Longmont, Colo.; Robert L. Fowlkes, Milton, Fla.

[73] Assignee: Air Products and Chemicals, Inc., Allentown, Pa.

[21] Appl. No.: 366,517

[22] Filed: Apr. 8, 1982

Related U.S. Application Data

[63] Continuation-in-part of Ser. No. 130,782, Mar. 17, 1980, abandoned.

[51] Int. Cl.$^4$ .................. C07D 265/30; C07D 295/02
[52] U.S. Cl. ...................................... 544/106; 544/87; 544/177
[58] Field of Search ......................................... 544/106

[56] References Cited

U.S. PATENT DOCUMENTS

| | | | |
|---|---|---|---|
| 2,412,209 | 12/1946 | Dickey et al. | 544/106 |
| 2,529,923 | 11/1950 | Dickey et al. | 544/106 |
| 3,151,112 | 9/1964 | Moss | 544/106 |
| 3,151,113 | 9/1964 | Advani et al. | 544/106 |
| 3,154,544 | 10/1964 | Langdon et al. | 544/106 |
| 3,155,657 | 11/1964 | Bedoit, Jr. | 544/106 |
| 4,091,218 | 5/1978 | Advani | 544/106 |

FOREIGN PATENT DOCUMENTS 46-32188  9/1971  Japan.
1530570  11/1978  United Kingdom.

OTHER PUBLICATIONS

Satterfield, *A. I. Ch. E. Journal*, vol. 21 (1975), pp. 209–228.
Ross, *Chemical Eng. Progress*, vol. 61(1965), pp. 77–82.
Satterfield et al, *A. I. Ch. E. Journal*, vol. 15(1969), pp. 226–234.
Dudukovic et al, "Catalysts Effectiveness Factor in Trickle Bed Reactors", pp. 387–388.
"Industrial Engineering Chemical Fundamentals", vol. 9, Nov. 9, 549–564 (1970), Zellner et al.

*Primary Examiner*—Robert W. Ramsuer
*Attorney, Agent, or Firm*—Russell L. Brewer; E. Eugene Innis; James C. Simmons

[57] ABSTRACT

This invention relates to an improved process for producing morpholine and its derivates by reacting ammonia and dialkylene glycol. The improvement resides in continuously charging the dialkylene glycol and ammonia to a trickle bed reactor, operating the reactor under conditions such that the dialkylene glycol is maintained as a discontinuous liquid phase and the morpholine formed is predominantly in the vapor phase.

13 Claims, 2 Drawing Figures

SYNTHESIS OF HETEROCYCLIC AMINES VIA THE REACTION OF DIALKYLENE GLYCOL AND AMMONIA

CROSS-REFERENCE TO RELATED APPLICATION

This application is a continuation-in-part of Ser. No. 130,782 having a filing date of Mar. 17, 1980, now abandond, the subject matter of which is incorporated by reference.

TECHNICAL FIELD

This inventon relates to the production of heterocyclic amines by the reaction of dialkylene glycol and ammonia. Morpholine, in particular, is synthesized by the reaction of diethylene glycol and ammonia.

DESCRIPTION OF THE PRIOR ART

U.S. Pat. No. 2,412,209 discloses a process for producing aliphatic amines from alcohols and particularly morpholine by the reaction of diethylene glycol and ammonia. Temperatures from 160°–400° C. are used and the reaction is carried out in the presence of a hydrogenation catalyst. Examples of hydrogenation catalysts suited for the reaction include Raney nickel, copper chromite, copper-nickel-chromite, iron, cobalt, etc. Liquid or gas phase conditions are suggested.

U.S. Pat. No. 3,154,544 discloses the preparation of substituted morpholines by the vapor phase conversion of a dialkylene glycol having at least one secondary hydroxyl group with hydrogen, and ammonia, in the presence of a hydrogenation/dehydrogenation catalyst. It is noted in the reference that diethylene glycol could not be converted to morpholine by reaction with ammonia in substantial conversion or yield, particularly under conditions suggested in the prior art e.g. U.S. Pat. Nos. 2,412,209 or 2,529,923.

U.S. Pat. No. 3,155,657 discloses a process for producing polyglycolamines and morpholine by the reaction of diethylene glycol and ammonia. Temperatures of 150°–350° C., pressures of 20–500 atmospheres and a contact time of from 5 minutes to 4 hours are suggested with pressures of 1000–3300 psig being used. The reaction was carried out preferably in the presence of a ruthenium catalyst. Yields of morpholine ranged from about 14–77% with glycol conversions of from about 48–96%.

U.S. Pat. No. 3,151,112 shows a process for producing morpholine and derivatives by the reaction of dialkylene glycols, e.g. diethylene glycol with ammonia at temperatures of 150°–400° C., and pressues of 30–400 atmospheres while maintaining liquid phase conditions. Ammonia is added in large excess to that of stoichiometric requirements. Yields of up to about 50% morpholine at the high reaction pressures are shown.

U.S. Pat. No. 3,151,113 discloses a process of preparing N-alkyl morpholine products by the reaction of hydroxy or amino terminated diethylene ether feedstocks with ammonia in the presence of a hydrogenation catalyst under liquid phase conditions. Pressures of 500–5,000 psig and temperatures of 150°–300° C. are employed. Conventional hydrogenation/dehydrogenation catalysts are used and these may be supported on alumina, kieselguhr, and other various supports or unsupported.

Japanese Patent Publication No. 46-32188, discloses a process for producing morpholine by the reaction of diethylene glycol and ammonia. In carrying out the process the reactants are charged to an autoclave and reacted at 240° C. and 25 atmospheres in the presence of hydrogen. The improved process relates to the use of a Raney-nickel catalyst having sufficient aluminum therein to consume by-product water as it is produced. The effect of water removal is to extend the catalyst life of the Raney-nickel.

U.S. Pat. No. 4,091,218 discloses a process for recovering ammonia from a gas stream resulting from the catalytic reaction of ammonia and a dialkylene glycol as described in U.S. Pat. No. 3,151,112. In the process the recovery of the product is effected by contacting the reaction effluent gas stream containing unreacted hydrogen, ammonia, and methane with a dialkylene glycol feed stock under conditions for adsorbing ammonia and leaving anhydrous hydrogen and methane.

British Patent No. 1,530,570 discloses a process for producing 2-(2-aminoalkoxy)alkanol (AEE) and morpholine derivatives from ammonia and oxydialkanol under pressures sufficient to maintain liquid conditions. Temperature and pressure are controlled in order to vary the quantity of the 2-(2-aminoethoxy)ethanol and morpholine derivative produced. Temperatures generally are 200°–220° C. while gauge pressures of at least 700 psig are used. Ammonia to alkanol ratios of 6:1 are used, with the ammonia being in the anhydrous form. Hydrogen is added to maintain catalyst activity.

SUMMARY OF THE INVENTION

This invention relates to an improved process for forming heterocyclic amines particularly in the form of morpholine and its derivatives. The basic process comprises reacting a dialkylene glycol and ammonia in the presence of hydrogen and a hydrogenation/dehydrogenation catalyst at conventional temperatures. The improvement constituting the basis of the invention resides in continuously charging the reactants to a trickle-bed catalytic reactor, operating the reactor under conditions such that the dialkylene glycol is present as a discontinuous liquid phase and continuously removing product. Preferably the conditions are maintained such that the heterocyclic amine is predominately in the gas phase.

Several advantages are associated with the improved process of this invention as compared to the prior art. These include:

the reaction permits substantially complete conversion of the dialkylene glycol, particularly diethylene glycol in the manufacture of morpholine, thereby minimizing recovery problems and minimizing recycle;

the reaction conditions are moderate e.g. low pressures are used thereby resulting in an energy saving as compared to prior art processes operating under high pressure, liquid phase conditions; and high selectivity to the heterocyclic amine i.e. morpholine and its derivatives, with little formation of heavies in the form of polyamines, e.g. morpholino diethylene glycol (MDEG) and bis-morpholino diethylene glycol (BMDEG) is achieved.

DESCRIPTION OF THE PREFERRED EMBODIMENTS

Figure 1:
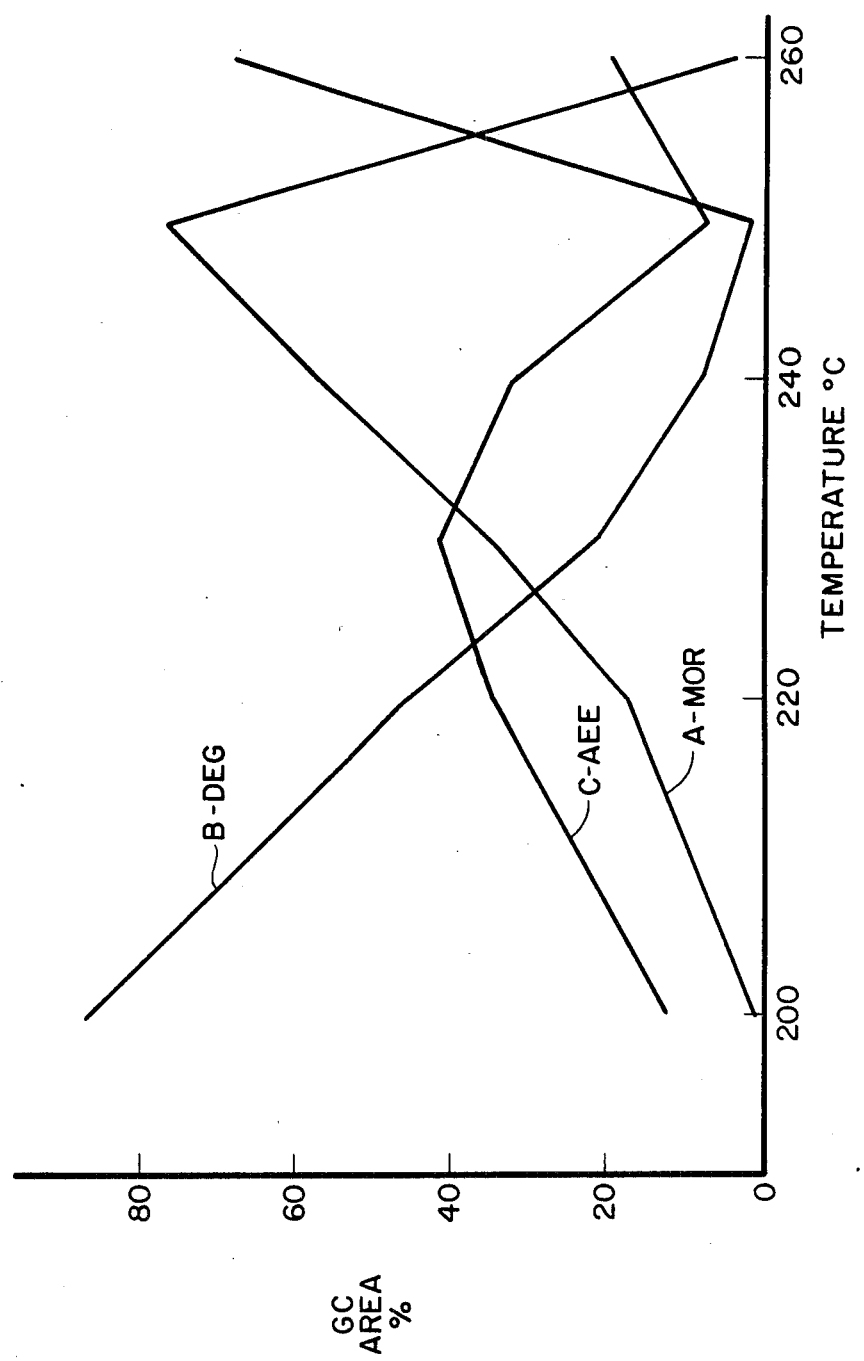
FIG. 1 is a plot of the product distribution in gas chromatograph area percent obtained by the reaction of diethylene glycol and ammonia versus temperature.

The feed component suited for practicing the process is a dialkylene glycol of the formula

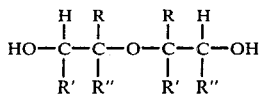

where R, R', and R" may be identical or different, each representing a hydrogen atom, alkyl or phenyl radicals. R, R', and R" contain typically from 1 to 6 carbon atoms, if alkyl, and preferably not more than 2 carbon atoms. For purposes of producing a commercially important heterocyclic amine, i.e. morpholine, the dialkylene glycol is diethylene glycol (DEG). Others, result in the production of alkyl and phenyl substituted morpholine derivatives. Specific examples of preferred dialkylene glycols include diethylene glycol, dipropylene glycol, dibutylene glycol, etc.

As with other processes, the reaction of dialkylene glycol to form heterocyclic amines is carried out in the presence of ammonia. Ammonia to dialkylene glycol ratios, on a molar basis, are at least 1:1 and up to 100:1, but preferably about 4 to 16:1. While the process requires at least equal molar amounts of ammonia to glycol to permit reaction on a stoichiometric basis, molar ratios higher than about 16 to 20:1 do not result in significant advantages. Because of the unique nature of the reaction conditions for carrying out the process, higher ratios of ammonia to glycol can have a detrimental effect in commercial units in that such higher ratios require increased pressures.

The presence of hydrogen is necessary for the proper and efficient conduct of the process. It is used in combination with ammonia and it is believed its function is to maintain catalyst activity. Molar ratios of ammonia to hydrogen generally are from about 4 to 60:1 and preferably about 6 to 32:1. Low ratios of ammonia to hydrogen, e.g. 2:1 to about 4:1 generally result in increased heavies formation. It is believed lower ammonia to hydrogen ratios reduce the ammonia content in the liquid phase thereby permitting any residual liquid phase morpholine to react and form heavies. Such is also true with the introduction of other inert gases such as nitrogen or methane. They, like hydrogen, reduce the ammonia content in the liquid phase. Therefore, it is preferred to use the minimum amount of hydrogen necessary to maintain the catalyst in the reactive state.

The catalysts suited for practicing the invention include those commonly used in prior art processes provided that they are wettable with the dialkylene glycol under the reaction conditions. By wettable, it is meant the catalyst will permit the formation of a very thin, liquid film about the surface of the catalyst as required in a trickle bed. The hydrogenation/dehydrogenation catalysts suited for practicing the process generally includes one or more metals from the group consisting of copper, nickel, cobalt, chromium, molybdenum, manganese, platinum, palladium, ruthenium, and rhodium. The preferred catalysts i.e. those which are most effective for the reactant are nickel, cobalt, and copper or contain such components.

Most of the above hydrogenation/dehydrogenation metals, even in highly porous form, will not permit the formation of thin film of dialkylene glycol about its surface, but rather will cause it to bead up on the surface. In those cases, the metal should be impregnated or incorporated into a wettable support. The support for the hydrogenation-dehydrogenation catalyst then is (a) one which is inert to the extent that it is not soluble or reactable with the reaction medium and (b) one which is wettable by the dialkylene glycol. Supports suited include silica, alumina, kieselguhr, and others conventionally used in the art. Alumina and silica are preferred. Broadly, the proportion of hydrogenation/dehydrogenation metal by weight of the catalyst, including support, is from about 0.01% to 70% and typically between 20 to 40%. This level may vary to the extent the catalyst loses its wettability.

In practicing the process, the temperature and pressure are maintained in the catalytic reaction zone such that some, at least about 1% preferably at least 5%, of the reactant dialkylene glycol is in the liquid phase, while the heterocyclic product is predominately in the vapor phase, e.g. greater than 80 mole % and preferably 90% assuming 90% conversion of the dialkylene glycol and 75% of the intermediate if one is formed. In addition, the temperature and pressure are selected so the reaction conditions do not substantially exceed (greater than about 10° C.) the dew point temperature of the feed.

In a preferred mode for carrying out the process, i.e., that of maintaining some of the dialkylene glycol in the liquid phase with the predominant portion of the heterocyclic amine in the vapor phase, the reactants are fed downflow through a reactor at a rate such that the dialkylene glycol is present as a discontinuous liquid phase. This rate inhibits flooding of the bed and hold up of gaseous product which is characteristic of those reactors known as trickle-bed reactors. Using this technique, the conversion of dialkylene glycol to a morpholine derivative is high and the percentage of heavies in the form of polyamines (MDEG and BMDEG) is low.

While not intending to be bound by theory, it is believed the presence of the 2 phase system between dialkylene glycol reactant and product amine in the trickle bed reactor permits high conversion of dialkylene glycol and high selectivity with little formation of heavies. The reaction between dialkylene glycol and ammonia occurs in the liquid phase. Because of the inherent attraction of the dialkylene glycol and ammonia via wetting of the catalyst surface, the actual contact time of the dialkylene glycol in the reaction zone is extended. On the other hand, as the dialkylene glycol is reacted to heterocyclic amine and because conditions in the reactor are such that the heterocyclic amine is predominately in the vapor phase it is rapidly removed from the reaction zone and in effect, has a short contact time. Therefore, since the hetercyclic amine concentration in contact with diethylene glycol in the liquid phase is relatively short, the heterocyclic amine is effectively precluded from reacting with the dialkylene glycol to form heavies. In addition, the reaction rate is enhanced because the reaction conditions also provide for expulsion of water, in addition to the gas phase morpholine, thus shifting the equilibrium to product.

When one operates under higher pressure, e.g. greater than about 500 psig when reacting diethylene glycol and ammonia, morpholine becomes part of the liquid phase, at least in a proportion greater than 40% at conventional operating temperatures, and thus its concentration in the reaction zone is increased and available for reaction with the DEG. In the prior art, then, the only way to reduce the amount of heavies was to increase the pressure substantially and increase the concentration of ammonia vis-a-vis morpholine in the liquid phase reaction zone. A higher mole ratio of ammonia to morpholine in the liquid phase reduces the possibility of the product morpholine reacting with DEG to form heavies.

To design the process for operating under the more favorable conditions, the liquid-vapor phase properties of the product are calculated assuming 90% dialkylene glycol conversion and 71% intermediate conversion for the major components present in the process (e.g. present as a feed or product mixture). These conversion values are selected since these are representative of the actual process conditons in the more desirable runs. However, as the feed conditions approach the dew point, conversion may be much lower than the assumed value. To gain a better idea of the actual liquid-vapor conditions, it may be necessary to select a lower value, approximating the degree of conversion, e.g. 50%, is more characteristic of the actual conversion observed. Using that value, one has a better understanding of the actual vapor-liquid equilibrium conditions.

In the case for producing morpholine, these major components are diethylene glycol, ammonia, hydrogen, 2-(2-aminoethoxy) ethanol (AEE intermediate) and by-products, e.g. morpholino diethylene glycol (MDEG) and bis-morpholino diethylene glycol (BMDEG). The liquid-vapor phase properties for the feed are based upon the feed components themselves. The vapor-liquid equilibrium for feed and products is determined from the equation:

VAPOR-LIQUID EQUILIBRIA $$\phi_I Y_I P = \gamma_I X_I F^\circ{}_I e^{\frac{(P\bar{V}_I)}{RT}}$$

$\phi_I$ = VAPOR FUGACITY COEFFICIENT
$\gamma_I$ = LIQUID ACTIVITY COEFFICIENT
$F^\circ{}_I$ = STANDARD STATE LIQUID FUGACITY
$\bar{V}_I$ = LIQUID PARTIAL MOLAR VOLUME
e = NATURAL BASE $$K_I = \frac{Y_I}{X_I} = \frac{\gamma_I F^\circ{}_I e^{(\frac{P\bar{V}_I}{RT})}}{\phi_I P}$$

The fugacity coefficient is solved by the use of the Virial equation of state and its application can be found in an article by Zellner et al, appearing in "Industrial Engineering Chemical Fundamentals", volume 9, Nov. 9, 549–564 (1970), which is incorporated by reference.

The standard state liquid fugacity is defined in the following equation:

STANDARD STATE LIQUID FUGACITY $$F^\circ{}_I = \frac{\phi_{IS} P_S}{e^{(\frac{P_S \bar{V}}{RT})}}$$

wherein $\phi_I$ is the pure component vapor phase fungacity coefficient, Ps is the pure component vapor pressure, e is natural base. This expression can be used where actual vapor pressure data are known. Otherwise a generalized correlation of the form below is used.

GENERALIZED CORRELATION $$\frac{F^\nu}{P_c} = F(T_R, W)$$

$P_c$ = CRITICAL PRESSURE
$T_R$ = REDUCED TEMPERATURE
$W$ = ACENTRIC FACTOR

The Generalized Correlation and its use is discussed in the Zellner et al article.

The UNIQUAC Model equation is used to calculate the activity coefficient. The equation model for a binary system is:

UNIQUAC EQUATION $$LN\gamma_I = LN\frac{\phi_I}{X_I} + \frac{Z}{2} Q_I LN\frac{\theta_I}{\phi_I} + \phi_J \left(L_I - \frac{R_I}{R_J} L_J\right) -$$

$$Q_I LN(\theta_I + \theta_J T_{JI}) + \theta_J Q_I \left(\frac{T_{JI}}{\theta_I + \theta_J T_{JI}} - \frac{T_{IJ}}{\theta_J + \theta_I T_{IJ}}\right)$$

$R_I$ = VOLUME PARAMETER OF MOLECULE I
$Q_I$ = AREA PARAMETER OF MOLECULE I
$\phi_I$ = VOLUME FRACTION OF MOLECULE I;
 $\phi_J$ REFERS TO MOLECULE J
$\theta_I$ = AREA FRACTION OF MOLECULE I
Z = COORDINATION NUMBER, SET EQUAL TO 10
T = ADJUSTABLE BINARY PARAMETER OBTAINED FROM REGRESSION OF VAPOR LIQUID EQUILIBRIUM DATA
 = LIQUID ACTIVITY COEFFICIENT
LN = NATURAL LOGARITHM $$L_I = \frac{Z}{2}(R_I - Q_I) - R_I - 1)$$

Activity coefficients for a multicomponent mixture can be determined from an extension of the equation model for a binary system using only binary adjustable parameters. No ternary (or higher) constants are required with this model. When vapor-liquid equilibrium data for individual binaries are not available, the adjustable binary parameters $T_{IJ}$'s are set equal to unity.

A description of the application of the UNIQUAC Model is found in Abrams et al, AICHE Journal, Volume 21, Number 116–128 (1975) and is incorporated by reference.

The reactions to product morpholine and by-products are believed to be as follows and provide a good reference for the discussion to follow regarding the reaction.

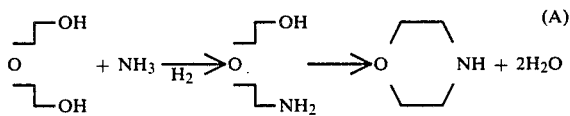

(A)

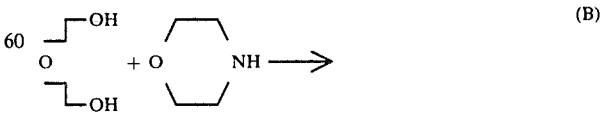

(B)

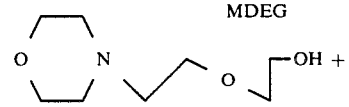

MDEG

-continued

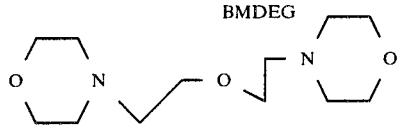

From the reaction formulas A and B, it can be postulated that selectivity to morpholine is largely dependent upon the concentration or ammonia and morpholine in the liquid phase and in contact with the ethylene glycol at the catalyst site. The increased concentration of ammonia shifts the reaction equilibrium to 2-(2-aminoethoxy) ethanol (intermediate) which then cyclizes and converts to morpholine. The removal of morpholine from the liquid phase also enhances selectivity because the morpholine is not available for reaction with the diethylene glycol or possibly 2-(2-aminoethoxy) ethanol or MDEG.

It is also postulated from the reaction formulas A and B that the process conditions facilitate a shift in reaction equilibrium toward the product in view of the fact that the morpholine, as well as the water, is removed via vaporization from the liquid reaction zone. Water inherently is vaporized under the specified conditions and it too is removed from the liquid reaction zone. In the past, this shift in reaction equilibrium was achieved by incorporating aluminum or other dehydrating component in the catalyst system. (NOTE: Japanese Patent Publication No. 46-32188.) The removal of the product morpholine from the reaction zone also shifts the equilibrium to increase conversion to the product side.

To permit the maintenance of an appropriate contact time in the reaction zone for the conversion of dialkylene glycol to the heterocyclic amine, the reaction is generally carried out at a liquid hourly space velocity of from 0.05 to 2.5 hr.$^{-1}$. (Liquid hourly space velocity (LHSV) is defined as the ratio of the volume of liquid dialkylene glycol per volume of catalyst per hour.) The liquid hourly space velocity is not as critical as some other parameters in the process in that it is largely dependent upon the activity of the catalyst. In those instances where the catalyst is highly reactive, a higher liquid hourly space velocity can be utilized to achieve greater throughput. Alternatively, where a catalyst having lower activity is used, lower space velocities are employed. Generally, liquid hourly space velocity is adjusted to permit the greatest conversion based on desired throughput. Commercially, it is possible to operate at a lower conversion and obtain greater product yield in view of the increased throughput through the reactor. Of course this will result in increasing the amount of by-product material coming from the reactor that must be recycled or recovered. A preferred LHSV range for cobalt or nickel containing catalysts is from about 0.2 to 1.0 hr.$^{-1}$.

The pressure used for the reaction is adjusted to meet desired vapor-liquid criteria for the reactants and products. In addition, the pressure must be adjusted to provide for a desired rate of reaction. Pressures generally suited for commercial operation are from 125 to 500 psig. However, pressures generally higher than 300 are not used as they show no significant improvement in the trickle bed reactor. Pressures above about 500 psig can result in increased heavies formation. Preferred pressures are about 200-300 psig.

The temperature used for carrying out the reaction generally is from about 140° to 280° C. at the pressure range specified. Of course as the pressure is increased, temperatures can be increased to the extent the vapor-liquid equilibrium criteria is met. Typically, the temperature used is from 200° to 250° C. Higher temperatures often cause coking of the catalyst or deactivation.

STATEMENT OF INDUSTRIAL APPLICATION

This invention relates to a process for making heterocyclic amines, particularly morpholine. The products have wide usage as corrosion inhibitors, or as intermediates for synthesizing antioxidants, herbicides and insecticides.

The following examples are representative of the preferred embodiments of the invention.

EXAMPLE 1

Runs of different feedstocks and under different conditions were made in a process design unit reactor which consisted of 0.41 inch (I.D.) 304 stainless steel tubing encased in aluminum block. The reactor was Model R-100 designed by the Ace Catalyst Company. The reactor utilized electrical heat for temperature control.

In the runs, diethylene glycol, ammonia and hydrogen were passed over a catalyst containing 42% nickel oxide carried on a gamma alumina support. The catalyst was crushed and sized to 12-18 mesh. The nickel oxide was reduced at 750° F. with hydrogen. The surface area was approximately 190 m$^2$ per gram and was supplied under the trademark HSC-102B by the Houdry Division of Air Products and Chemicals, Inc. The reactor was charged with 10 cc catalyst to provide a reactor zone bed depth of about 10 centimeters.

In the process the reactor was operated at a variable LHSV based on diethylene glycol as well as variable hydrogen to diethylene glycol to ammonia molar feed ratios. Hydrogen feed rates were measured in ml/min. at STP whereas ammonia and DEG were measured in ml/hr. Product distribution is given in gas chromatograph area percent.

The feed DEG, including NH$_3$ and H$_2$ was passed downflow through the reactor at various temperatures ranging from 190°-260° C. The liquid DEG remained in the discontinuous phase. These feed conditions are characteristic of those utilized to maintain trickle-bed conditions in a trickle-bed reactor. Conversion results are shown in Table I and the vapor-liquid data for some of the runs are shown in Table 2. DEG represents diethylene glycol, MOR represents morpholine and AEE represents 2-(2-aminoethoxy) ethanol. The liquid-vapor equilibrium values were calculated assuming 90% diethylene glycol conversion and 71% AEE conversion.

With respect to Table 2, K represents the value for a component as previously described in the formula. The values for DEG and NH$_3$ are the moles liquid for these components at the reaction conditions. L/F refers to the total moles liquid at feed conditions divided by total moles feed and is expressed in percent; NH$_3$/F refers to the ratio of ammonia in the liquid phase divided by the total moles feed. The values MOR and AEE vapors are the moles of each component in the vapor phase. Total moles product refers to the moles of DEG, MOR, AEE, water and ammonia that would be present assuming 90% conversion of DEG and 71% conversion of AEE. The value % MOR refers to the percent of morpholine in the vapor phase. NH$_3$/MOR refers to the ratio of the moles ammonia in the liquid product to the moles liquid morpholine in the Product. MOR refers to moles morpholine product in the liquid phase.

TABLE 1

| Run | Temp. °C. | (psig) Press. | ml/min STP H₂ | ml/hr DEG | ml/hr NH₃ | H₂/DEG/NH₃ Mole Ratio | (DEG) LHSV | MOR | AEE | DEG | MDEG | Others |
|---|---|---|---|---|---|---|---|---|---|---|---|---|
| 1 | 240 | 250 | 15 | 7.5 | 18 | 0.5/1/8 | 0.5 | 32 | 31 | 29 | 3.5 | 4.4 |
| 2 | 250 | 250 | 15 | 7.5 | 18 | " | 0.5 | 37 | 23 | 30 | 1.3 | 8.3 |
| 3 | 260 | 250 | 15 | 7.5 | 18 | " | 0.5 | 25 | 23 | 41 | 1.3 | 10 |
| 4 | 190 | 280 | 44 | 3.8 | 6.8 | 3/1/6 | 0.25 | 31 | 21 | 30 | 14 | 3.7 |
| 5 | 195 | 280 | 44 | 3.8 | 6.8 | " | 0.25 | 28 | 24 | 36 | 10.4 | 1.2 |
| 6 | 200 | 200 | 44 | 3.8 | 6.8 | " | 0.25 | 21 | 25 | 42 | 8.6 | 3.1 |
| 7 | 205 | 280 | 44 | 3.8 | 6.8 | " | 0.25 | 21 | 20 | 36 | 15 | 3.2 |
| 8 | 210 | 140 | 44 | 3.8 | 6.8 | " | 0.25 | 26 | 19 | 35 | 15 | 4.2 |
| 9 | 210 | 350 | 44 | 3.8 | 6.8 | " | 0.25 | 31 | 20 | 29 | 19 | 1.4 |
| 10 | 210 | 280 | 44 | 3.8 | 6.8 | " | 0.25 | 29 | 19 | 31 | 17 | 4.1 |
| 11 | 210 | 280 | 15 | 3.8 | 9.2 | 1/1/8 | 0.25 | 29 | 30 | 32 | 7.2 | 1.4 |
| 12 | 210 | 280 | 30 | 3.8 | 8.1 | 2/1/7 | 0.25 | 27 | 25 | 35 | 12 | 1.7 |
| 13 | 210 | 280 | 7.5 | 3.8 | 9.8 | 0.5/1/8.5 | 0.25 | 26.2 | 32 | 37 | 3.7 | 1.2 |
| 14 | 210 | 280 | 7.5 | 3.8 | 18.4 | 0.5/1/16 | 0.25 | 20 | 38 | 38 | 1.5 | 2.5 |
| 15 | 210 | 280 | 105 | 3.8 | 2.3 | 7/1/2 | 0.25 | 17 | 5.4 | 40 | 36* | 1.5 |
| 16 | 210 | 280 | 44 | 3.8 | 6.8 | 3/1/6 | 0.25 | 22 | 22 | 41 | 11 | 3.9 |
| 17 | 220 | 280 | 7.5 | 3.8 | 9.8 | 0.5/1/8.5 | 0.25 | 78 | 7.6 | — | 9.8** | 5.0 |
| 18 | 200 | 250 | 20 | 7.1 | 28 | 0.72/1/13 | 0.47 | 0.6 | 11 | 86 | 0.6 | 1.5 |
| 19 | 220 | 250 | 20 | 7.1 | 28 | " | 0.47 | 13 | 31 | 51 | 2.5 | 3.1 |
| 20 | 230 | 250 | 20 | 7.1 | 28 | " | 0.47 | 28 | 31 | 33 | 4.9* | 4.3 |
| 21 | 240 | 250 | 20 | 7.1 | 28 | " | 0.47 | 47 | 21 | 17 | 6.5* | 9.2 |
| 22 | 250 | 250 | 20 | 7.1 | 28 | " | 0.47 | 63 | 8.8 | 7.7 | 7.1* | 13 |
| 23 | 260 | 250 | 20 | 7.1 | 28 | " | 0.47 | 2.3 | 16 | 76 | 0.1 | 5.7 |
| 24 | 220 | 250 | 20 | 7.1 | 28 | " | 0.47 | 5.8 | | Catalyst Coked | | |
| 25 | 220 | 850 | 12 | 6.3 | 15 | 0.5/1/8 | 0.25 | 54 | 22 | 13 | 8.5 | 3.1 |
| 26 | 220 | 550 | 12 | 6.3 | 15 | 0.5/1/8 | 0.25 | 52 | 22 | 15 | 6.1 | 4.5 |
| 27 | 220 | 270 | 12 | 6.3 | 15 | 0.5/1/8 | 0.25 | 56 | 22 | 15 | 4.8 | 2.8 |
| British Patent 1,530,570 | | | | | | | | | | | Heavies | |
| 28 | 209 | 700 | — | — | — | 0.9/1/6.4$^V$ | 0.61 | 49 | 18 | 15 | 16 | 2.3 |
| 29 | 210 | 1400 | — | — | — | 0.9/1/6.34$^V$ | 0.59 | 45 | 20 | 26 | 7.0 | 2.1 |
| 30 | 210 | 2625 | — | — | — | 0.9/1/5.97$^V$ | 0.61 | 28 | 17 | 50 | 3.5 | 1.9 |

$^V$Reactor feed also includes 6.6 moles H₂O/mole DEG and 0.3 moles N₂/mole DEG.
*includes some BMDEG

TABLE 2

| Run | °C. Dew Point | K value NH₃ | Feed Moles Liq. DEG | Feed Moles Liq. NH₃ | L/F % | NH₃/F % |
|---|---|---|---|---|---|---|
| 1 | 266 | 7.01 | 0.56 | 0.084 | 6.9 | 0.8 |
| 4 | 273 | 5.84 | 0.93 | 0.154 | 12.2 | 1.54 |
| 8 | 244 | 10.6 | 0.6 | 0.04 | 7.94 | 0.48 |
| 9 | 283 | 5.03 | 0.89 | 0.16 | 12.3 | 1.6 |
| 10 | 273 | 5.98 | 0.86 | 0.12 | 11.2 | 1.24 |
| 11 | 269 | 5.54 | 0.85 | 0.16 | 10.6 | 1.6 |
| 12 | 270 | 5.75 | 0.85 | 0.14 | 10.9 | 1.45 |
| 13 | 268 | 5.4 | 0.84 | 0.17 | 10.4 | 1.78 |
| 14 | 249 | 5.3 | 0.71 | 0.15 | 5.6 | 0.88 |
| 15 | 281 | 7.1 | 0.89 | 0.04 | 13.0 | 0.4 |
| 16 | 273 | 5.98 | 0.86 | 0.12 | 11.2 | 1.2 |
| 20 | 250 | 6.6 | 0.48 | 0.07 | 3.8 | 0.53 |
| 21 | 250 | 7.0 | 0.28 | 0.04 | 2.2 | 0.27 |
| 22 | 250 | 7.3 | 0.017 | 0.002 | 0.13 | 0.016 |
| 23 | 250 | 7.3 | 0.0 | 0 | 0 | 0 |
| 25 | 321 | 2.3 | 0.94 | 0.66 | 17.6 | 6.9 |
| 26 | 299 | 3.2 | 0.9 | 0.37 | 14.0 | 3.9 |
| 27 | 268 | 5.9 | 0.79 | 0.14 | 10.1 | 1.4 |
| 28 | 319 | 2.7 | 0.96 | 0.52 | 19.5 | 6.3 |
| 29 | 378 | 1.7 | 0.98 | 1.3 | 31.1 | 15.0 |
| 30 | — | 1.24 | 0.998 | 4.01 | 67.8 | 48.4 |

| Run | Total Moles/Product | Moles Total Liq. | MOR | NH₃/MOR |
|---|---|---|---|---|
| 1 | 9.93 | 0 | — | — |
| 4 | 10.63 | 0.566 | 0.10 | 0.51 |
| 8 | 10.63 | 10.63 | 0.63 | — |
| 9 | 10.63 | 0.43 | 0.07 | 0.57 |
| 10 | 10.63 | 0.27 | 0.038 | 0.57 |
| 11 | 10.63 | 0.23 | 0.031 | 0.86 |
| 12 | 10.63 | 0.25 | 0.034 | 0.73 |
| 13 | 10.63 | 0.22 | 0.029 | 0.95 |
| 14 | 18.1 | — | — | — |
| 15 | 10.63 | 1.12 | 0.05 | 0.1 |
| 16 | 10.63 | 0.27 | 0.038 | 0.57 |
| 20 | 15.3 | 0 | — | — |
| 21 | 15.3 | 0 | — | — |
| 22 | 15.3 | 0 | — | — |
| 23 | 15.3 | — | — | — |
| 25 | 9.93 | 1.23 | 0.22 | 1.65 |
| 26 | 9.93 | 0.62 | 0.08 | 1.2 |
| 27 | 9.93 | 0.07 | 0.009 | 0.95 |
| 28 | 8.88 | 1.33 | 0.27 | 0.84 |
| 29 | 8.88 | 3.57 | 0.50 | 3 |
| 30 | 8.88 | 8.88 | 0.639 | 8.5 |

| Run | VAPOR MOR | VAPOR AEE | % MOR | K VALVE MOR | K VALVE NH₃ |
|---|---|---|---|---|---|
| 1 | 0.63 | 0.26 | 100 | | |
| 4 | 0.53 | 0.18 | 83.8 | 0.29 | 5.38 |
| 8 | — | — | 100 | 0.64 | 10.1 |
| 9 | 0.56 | 0.14 | 88.8 | 0.34 | 5.05 |
| 10 | 0.6 | 0.16 | 94 | 0.41 | 6.05 |
| 11 | 0.6 | 0.17 | 94.9 | 0.43 | 5.66 |
| 12 | 0.6 | 0.17 | 94.5 | 0.42 | 5.85 |
| 13 | 0.6 | 0.17 | 95.3 | 0.43 | 5.57 |
| 14 | 0.63 | 0.26 | 100 | 0.40 | 5.3 |
| 15 | 0.58 | 0.13 | 91.9 | 0.38 | 7.05 |
| 16 | 0.6 | 0.16 | 93.8 | 0.41 | 6.05 |
| 20 | 0.63 | 0.26 | 100 | 0.44 | 5.98 |
| 21 | 0.63 | 0.26 | 100 | 0.44 | 5.98 |
| 22 | 0.63 | 0.26 | 100 | 0.44 | 5.98 |
| 23 | 0.63 | 0.26 | 100 | 0.44 | 5.98 |
| 25 | 0.41 | 0.04 | 64 | 0.25 | 2.4 |
| 26 | 0.52 | 0.09 | 81.3 | 0.31 | 3.38 |
| 27 | 0.629 | 0.17 | 98.4 | 0.52 | 6.0 |
| 28 | 0.36 | 0.028 | 56.3 | 0.49 | 3.56 |
| 29 | 0.50 | 0.255 | 20.6 | 0.17 | 1.68 |
| 30 | — | — | 0 | 0.59 | 1.9 |

The following are general observations or trends shown in the series of reactions reported in Table I. First it should be noted that conversion of diethylene glycol to morpholine increases with increasing temperature, e.g., from 200°-250° C. as noted in runs 18-22, except where the temperature is increased to the point where substantially all of the reactants are in the gas phase, e.g. about 260° C. as noted in Run 23. At that point, i.e. when the reactants are above the dew point, (about 10° C.) the conversion of DEG to product morpholine tends to fall off dramatically.

FIG. 1, line A, is a graph which shows the increase of morpholine concentration beginning at 200° C. to 250° C. and then dropping off sharply at 250° C. to 260° C. Line B shows the concentration of diethylene glycol in the product at various temperatures. Its concentration generally decreases in proportion to the morpholine increase and then its concentration increases with the morpholine decrease at about 250° C. Line C is a plot of the 2-(2,aminoethoxy) ethanol concentration.

Table 2 shows the moles liquid DEG ranges from about 1.7% Run 22 to a maximum of about 90% (Run 4). Typically the range is about 1-60%.

Runs 1, 3, 12, 15-17 and particularly Runs 11-16 show the importance of keeping the ratio of ammonia to DEG high. All of these runs can be combined to show that as the molar ratio of ammonia to DEG is reduced, the proportion of heavies increases with the highest proportion being noted in Run 15. From the data, ammonia to DEG molar ratios within the range of about 4-16:1 provide reasonably good results.

The importance of ammonia ultimately in the liquid phase shows up in the $NH_3$/MOR ratio of Table 2. Selectivity to morpholine generally decreases as the $NH_3$/MOR ratio decreases (contrast run 15).

Runs 25, 26 and 27 as a group show the importance of keeping the pressure low to avoid the formation of heavy by-products. Yield loss to MDEG in the trickle-bed reactor nearly doubles when pressures are increased from 270-850 psig. Runs 28, 29 and 30 show the same trend, i.e., the increase of heavy formation but the effect is much less at the lower 140-350 psig level. On the other hand when operating under conditions where the diethylene gylcol is present as a continuous phase, e.g., Runs 29, 30 and 31 taken from Example 1 of British Patent No. 1,530,570 heavies concentration is reduced as pressure is increased. When comparing the vapor/liquid ratios for the runs of this invention, e.g. 25-27 versus 29-31, even though the processes are different there is a correlation with respect to the mole ratio of diethylene glycol, ammonia and morpholine in the liquid phase and the level of heavies production. For example, at pressures at about 700 psig the morpholine content in the liquid phase is highest and as the pressure is increased the percentage of morpholine in the liquid phase is reduced. (The results reported in Runs 29, 30 and 31 were recalculated making some assumptions to place them on the same basis as the other runs reported in Table 1.)

It should be noted that the numbers given for moles liquid and vapor etc. in Table 2 are not precise as they often are based upon assumptions for the adjustable binary parameters in the equations. However, the numbers do show trends. Greater precision is noted in the % MOR values because in those instances a small change in the moles morpholine in the liquid phase does not drastically affect the overall numerical value. As a result the data in Table 2 shows that where the % MOR is high e.g. greater than 90% (assuming about plus or minus 5%) the selectivity is much higher than where % MOR is lower e.g. 83%. Compare Runs 1 and 4.

EXAMPLE 2

The procedure of Example 1 was repeated except that a calcium promoted HSC 102B catalyst was used, the calcium being added by washing the HSC102B catalyst with aqueous calcium nitrate and then drying the catalyst. The conditions utilized in the reactions were: temperature 210° C., pressure 295 psig, and an LHSV based on the diethylene glycol of 0.25 hour$^{-1}$.

Figure 2:
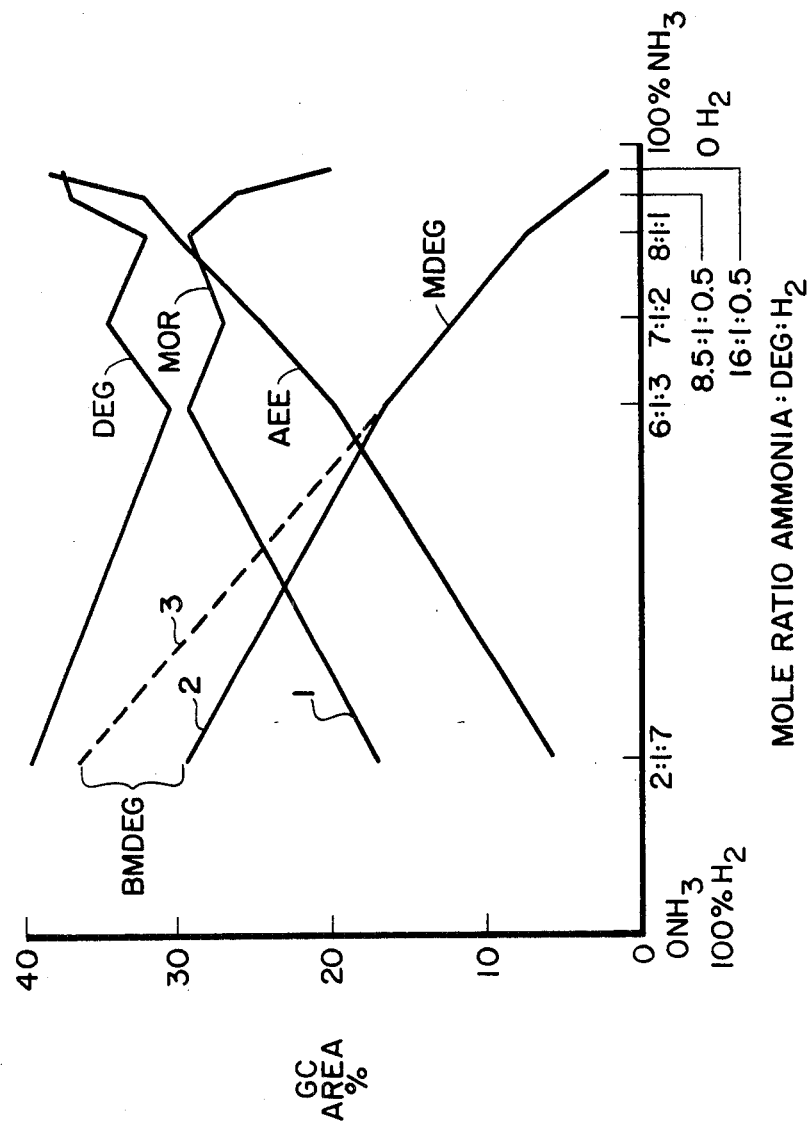
FIG. 2 is a plot of product distribution in gas chromotograph area percent versus ammonia-diethylene glycol-hydrogen mole concentration in the feed.

The ratio of $NH_3+H_2$/DEG was kept constant at 9 (except for Run 14 where it was 16.5) while the ratio of $NH_3$ plus $H_2$ was varied. FIG. 2 is a plot of some of the results in gas chromatograph area percent for selected components vs the mole ratio of ammonia to hydrogen as mole percent. Also provided are feed molar ratios of ammonia, diethylene glycol and hydrogen.

FIG. 2 shows, as did Example 1, that at low ammonia to feed diethylene glycol mole ratios, conversion to morpholine is relatively low. Morpholine conversion (line 1) increases gradually as the molar ratio of ammonia to diethylene glycol increases, and at a mole ratio of from about 6 to 9 moles ammonia per mole diethylene glycol conversion levels off.

MDEG and BMDEG by-product is represented by line 2, and if one were the extrapolate line 2 to include all heavies, essentially a straight line relationship would be noted as shown in line 3. This data also shows that heavies concentration can be reduced for a given reaction condition by increasing the ammonia concentration.

EXAMPLE 3

The procedure of Example 1 was repeated except that a temperature of 220° C., a pressure of about 250 psia, and a feed ratio of 8:1:0.5 of ammonia:DEG,$H_2$ was utilized. The variable was residence time and that was varied from an LHSV of 1 to a low of 0.25 hours$^{-1}$. The results are presented in Table 3.

TABLE 3

Effect of Residence Time on Morpholine Yield and Production Rate
Catalyst = HSC-102B
Mole Ratio $NH_3$:DEG:$H_2$ = 8:1:0.5

| DEG LHSV | MOR Selectivity | MOR Single Pass Yield | Production Rates, g/cc/hr. | | | |
|---|---|---|---|---|---|---|
| | | | MOR | DGA | DEG | X's |
| 0.5 | 91 | 69 | 0.31 | 0.11 | 0.005 | 0.047 |
| 0.25 | 87 | 77 | 0.17 | 0.024 | 0.003 | 0.037 |
| 1.0 | 97 | 32 | 0.29 | 0.53 | 0.185 | 0.031 |
| 0.5 | 93 | 56 | 0.25 | 0.14 | 0.059 | 0.035 |

The above results show that selectivity to morpholine decreases with decreasing space velocity. Conversion on the other hand increases with decreasing space velocity. The data also shows that good single space yields are possible with this process. (X's represents by-product.)

EXAMPLE 4

Comparative Example

A series of runs were carried out in accordance with the proess of Example 1 except that the feed was introduced upflow through the reactor. Under these conditions the diethylene glycol was present as a continuous phase in an effort to approximate the conditions of Example III in U.S. Pat. No. 3,151,112. The same catalyst HSC 102B was used for all runs. Table 4 lists the comparative conditions and results for these runs and the results obtained.

TABLE 4

| Run | Temp. °C. | (psig) Press. | H₂/DEG/NH₃ Mole Ratio | (DEG) LHSV | DEG Conversion | Concentration GC area % | | | |
|---|---|---|---|---|---|---|---|---|---|
| | | | | | | MOR | AEE | TUL | Heavies |
| 1 | 220 | 850 | 0.5/1/8 | 0.25 | 81 | 56 | 21 | 8 | 15 |
| 2 | 220 | 270 | " | 0.25 | 49 | 42 | 32 | 12 | 14 |
| 3 | 220 | 270 | " | 0.25 | 33 | 23 | 51 | 15 | 12 |
| 4 | 220 | 550 | " | 0.25 | 51 | 43 | 41 | 7 | 10 |
| 5 | 220 | 870 | " | 0.25 | 64 | 48 | 34 | 5 | 12 |

What we claim is:

1. In a process for producing a heterocyclic amine by the reaction of a dialkylene glycol of the formula

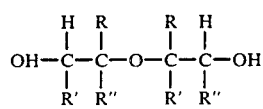

where R, R', R" may be identical or different each representing a hydrogen atom, alkyl or phenyl radicals, and ammonia in a fixed bed catalytic reactor said reactions being carried out in the presence of hydrogen and a hydrogenation-dehydrogenation catalyst the improvement which comprises:

passing the dialkylene glycol and ammonia downflow through said reactor at a temperature and pressure such that at least 1% of the dialkylene glycol is maintained in the liquid phase, said dialkylene glycol and ammonia being passed through said reactor at a rate such that the dialkylene glycol is present in said reactor as a discontinuous liquid phase; and said reactor being operated such that any heterocyclic amine formed during the reaction is predominately in the vapor phase;

and continuously removing heterocyclic amine product from the reactor.

2. The process of claim 1 wherein said dialkylene glycol is diethylene glycol.

3. The process of claim 2 wherin the temperature maintained in the reactor is from about 140° to 280° C.

4. The process of claim 3 wherein the pressure maintained in the reactor is from about 125 to 500 psig.

5. The process of claim 4 wherein the liquid hourly space velocity, based on dialkylene glycol feed, is from about to 0.05 to 2.5.

6. The process of claim 5 wherein the hydrogenation-dehydrogenation catalyst is wettable by the dialkylene glycol and is carried on a support selected from the group consisting of alumina, silica, and mixtures thereof.

7. The process of claim 6 wherein said hydrogenation-dehydrogenation catalyst carried upon the support contains a component selected from the group consisting of nickel, cobalt and chromium.

8. The process of claim 7 wherein said hydrogenation-dehydrogenation catalyst is a nickel catalyst supported on alumina.

9. The process of claim 4 wherein said reaction zone is maintained at about 200°–250° C. and the pressure is from 200–300 psig.

10. The process of claims 2, 4, 5, 6 or 9 wherein the heterocyclic amine is morpholine and at least 90% of the total moles morpholine in the product is in the vapor phase.

11. The process of claim 5 wherein the ammonia to hydrogen ratio is from 6–32:1, and the ratio of ammonia to diethylene glycol is from 4–16:1.

12. In a process of producing morpholine by the reaction of diethylene glycol and ammonia in a reactor, said reaction being carried out in the presence of hydrogen and hydrogenation-dehydrogenation catalyst, the improvement which comprises:

passing said ammonia and diethylene glycol downflow through a tubular reactor packed with said hydrogenation/dehydrogenation catalyst, said passing being at a rate to provide a liquid hourly space velocity, based on diethylene glycol, of 0.5–2.5 hours⁻¹;

establishing a mole ratio of ammonia to hydrogen from 6–32:1 and an ammonia to diethylene glycol ratio of about 4–16:1 in said reactor;

operating the reactor within a temperature range of 140°–280° C. and a pressure range of from about 125–500 psig, such temperature and pressure being controlled within such range that at least 5% of the diethylene glycol is in the liquid phase; and further, any morpholine formed is predominately in the vapor phase; and removing morpholine product from the reactor.

13. The process of claim 12 wherein the hydrogenation-dehydrogenation catalyst is carried on a support selected from the group consisting of alumina, silica and mixtures thereof and the support contains a component selected from the group consisting of nickel, cobalt and chromium.

* * * * *